United States Patent [19]

Jayaraman

[11] Patent Number: 5,922,393
[45] Date of Patent: Jul. 13, 1999

[54] MICROPOROUS COVERED STENTS AND METHOD OF COATING

[76] Inventor: Swaminathan Jayaraman, 106/18 11th B Cross (10th & 11th Main) Malleswaram, Bangalore — 560003, India

[21] Appl. No.: 09/110,225
[22] Filed: Jul. 6, 1998

Related U.S. Application Data

[62] Division of application No. 09/008,700, Jan. 19, 1998., which is a division of application No. 08/689,290, Aug. 6, 1996., Pat. No. 5,713,949

[51] Int. Cl.⁶ .............................. B05D 1/00; B05D 3/12; A61L 27/00
[52] U.S. Cl. .......................... 427/2.3; 427/2.25; 427/2.28
[58] Field of Search .................. 427/2.25, 2.28, 427/2.3, 430.1

[56] References Cited

U.S. PATENT DOCUMENTS

| 5,234,457 | 8/1993 | Andersen | 606/198 |
|---|---|---|---|
| 5,330,500 | 7/1994 | Song | 606/198 |
| 5,344,426 | 9/1994 | Lau et al. | 606/198 |
| 5,443,499 | 8/1995 | Schmitt | 623/1 |
| 5,449,382 | 9/1995 | Dayton | 623/1 |
| 5,534,287 | 7/1996 | Lukic | 427/2.25 |
| 5,537,729 | 7/1996 | Kolobow | 427/2.3 |
| 5,578,075 | 11/1996 | Dayton | 623/1 |
| 5,713,949 | 2/1998 | Jayaraman | 623/1 |
| 5,837,313 | 11/1998 | Ding et al. | 427/2.25 |

Primary Examiner—Diana Dudash
Attorney, Agent, or Firm—Larson & Larson, P.A.; James E. Larson

[57] ABSTRACT

A coated microporous stent and method of coating are disclosed. The inventive stent consists of a tubular member made from a flat sheet assembled together in a tube with the ends of the sheet assembled together through a technique such as surface fusing. Preferably, the stent is made up of a plurality of spaced rows of slots with spaces between adjacent slots within a row staggered with respect to corresponding spaces on adjacent rows. In a first embodiment of a coated stent, a coating is attached to the stent only at a single area of line contact on the outer surface of the stent with the remainder of the coating being larger than the unexpanded stent, but being made of dimensions designed to snugly receive the outer surfaces of the stent when it is expanded within a blood vessel. In a second embodiment, the present invention also contemplates coating of a stent of the type known as a "self-expanding" stent that is programmed to self-expand at a particular temperature by either using the shape memory properties of the metal or by using the flexibility and elasticity of the metal. In this embodiment, prior to programming the formed stent, the stent is placed in a container of coating material and is coated. Thereafter, the stent is programmed in the desired manner and is subsequently physically compressed and kept inside a sheath. The stent is placed within the blood vessel still within the sheath, and the sheath is then removed, allowing the stent to expand to its desired configuration. Methods of making such coated stents are disclosed.

7 Claims, 11 Drawing Sheets

MICROPOROUS COVERED STENTS AND METHOD OF COATING

This application is a divisional from application Ser. No. 09/008,700, filed Jan. 19, 1998, which is a divisional of Ser. No. 08/689,290, filed Aug. 6, 1996, now U.S. Pat. No. 5,713,949.

BACKGROUND OF THE INVENTION

The present invention relates to a covered microporous stent and method of coating. Coated stents are known as are stents that are designed to expand at the site within a blood vessel where they are intended to engage the internal wall of the blood vessel to reinforce it.

Currently available stents are known to cause restenosis. Restenosis can be caused by incompatibility of the metallic surface of the stent that engages the inner walls of the blood vessel giving rise to subacute thrombosis, usually within four weeks of implantation of the stent. Another possible cause of restenosis is the recoil of the metallic surface of the stent when placed along the internal wall of the artery. Such recoil does not occur immediately, but, rather, when the stent pulses due to its elastic nature, stresses act downwardly toward the stent resulting in gradual diminishing of the luminal diameter.

Additionally, most commercially available stents have an open mesh area when they are expanded and rapid ingrowth of collagen cells and smooth muscle cells gradually occurs through these open areas. Collagen cells contributing toward intimal hyperplasia eventually result in the narrowing of the lumen diameter. Additionally, sometimes, at the location where the stent is to be placed, such as, for example, in saphenous vein grafts, thrombus exists that must be bypassed. Finally, in the aorta and peripheral arteries, a large portion of the aneurysmal sac may have to be bypassed prior to stent implantation.

Use of polymeric or biologic material to coat a stent is generally known. However, in such coated stents, when they are expanded within a blood vessel, the coefficient of expansion of the coating greatly differs from that of the expanding stent such that, upon expansion, the surface of the coating tears rendering the expanded stent uncoated. If, as a solution, the coating is applied more thickly, such a thick coating can deter stent expansion or can have such a high profile that implantation into the body is difficult. The same problem occurs when a stent is coated by sandwiching it between inner and outer coating layers. If the stent cannot be expanded to its full intended diameter, the success of the implantation can be drastically compromised.

While the prior art does describe the concept of providing a stent with a coating, Applicant is unaware of any prior art that specifically describes whether such a coating surrounds the individual members of the metallic stent or whether such a coating covers all of the gaps between the various interstices of the expanded stent.

The prior art also describes biologic coatings such as collagen gelatin to be employed on a balloon expandable or thermally expandable stent. To coat such a stent, it is placed in a mandrel and then dipped into the biologic solution and then dried in an oven. Applicant is unaware of the nature of the resulting properties of the stent when expanded.

Applicant is also aware that stents have been coated with a polymeric material such as silicone that renders the resulting stent impervious to any incursion of biologic tissue. However, in such stents, the impervious nature of the coating deters the healing of the surrounding tissues.

The following prior art is known to Applicant:
U.S. Pat. No. 5,234,457 to Andersen
U.S. Pat. No. 5,330,500 to Song
U.S. Pat. No. 5,344,426 to Lau et al.
U.S. Pat. No. 5,443,499 to Schmitt.

None of these patents teaches the features and aspects of the present invention as set forth hereinbelow, including the particular stent coatings nor the method of so coating a stent.

SUMMARY OF THE INVENTION

The present invention relates to a polymer or biological material coated microporous stent and method of coating. The present invention includes the following interrelated objects, aspects and features:

(1) In a first aspect, in the preferred embodiments of the present invention, the inventive stent consists of a tubular member made from a flat sheet assembled together in a tube with the ends of the sheet assembled together through a technique such as surface fusing by employing means such as plasma energy, LASER or ultrasound. Preferably, the stent is made up of a plurality of spaced rows of slots with spaces between adjacent slots within a row staggered with respect to corresponding spaces on adjacent rows.

(2) In a first embodiment of a coated stent, a coating is attached to the stent only at a single area of line contact on the outer surface of the stent with the remainder of the coating being larger than the unexpanded stent, but being made of dimensions designed to snugly receive the outer surfaces of the stent when it is expanded within a blood vessel.

(3) In the method of making the above-described coating, the unexpanded stent is placed over a mandrel and is then inserted within an elongated recess eccentrically located within a larger mandrel with the recess having an elongated opening on a peripheral edge thereof. When the stent so assembled to the mandrels is covered with the coating, the coating surrounds the outer mandrel and connects with the stent only at the area of the peripheral linear opening. When the mandrels are removed, what remains is the stent having an enlarged coating attached thereto only at one linear elongated location. This embodiment is practiced concerning a stent that is intended to be expanded through the use of expansion means such as, for example, a balloon catheter or a mechanical expanding tool.

(4) The present invention also contemplates coating of a stent of the type known as a "self-expanding" stent that is programmed to self-expand at a particular temperature by either using the shape memory properties of the metal or by using the flexibility and elasticity of the metal. In this embodiment, prior to programming the formed stent, the stent is placed in a container of coating material and is coated. Thereafter, the stent is programmed in the desired manner and is subsequently physically compressed and kept inside a sheath. The stent is placed within the blood vessel still within the sheath, and the sheath is then removed, allowing the stent to expand to its desired configuration.

The present invention is intended to fulfill the following objects, aspects and features:

(1) To develop an ultrathin thin coating on a stent that is so configured that, when the stent is expanded, the outer expanded diameter of the stent is equal to the inner wall diameter of the coating with the structure of the coating being uncompromised.

(2) The coating so developed has the property of microporosity that facilitates controlled ingrowth of tissue within the coating to provide a neoinitimal healing mechanism.

(3) The coating may be provided with specific substances that are designed to enhance the healing properties of the stent.

(4) The wall thickness of the coating is intended to be extremely thin, on the order of 5 to 80 mils in thickness. For larger diameters the thickness of the coating can be up to 100 mils thick.

(5) The coating provides a conduit for dilatation of the plaque, can bypass a thrombus or eliminate an aneurysmal sac.

It is a further object to provide a plurality of such stents attached together in a manner to be described in greater detail hereinafter. In this regard, the length of the coating and the stent may be varied so that the stent runs some or all of the entire length of the microporous coating. Additionally, if desired, the stent may be intermittently placed within the coating or may be placed at only the proximal and distal ends thereof.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
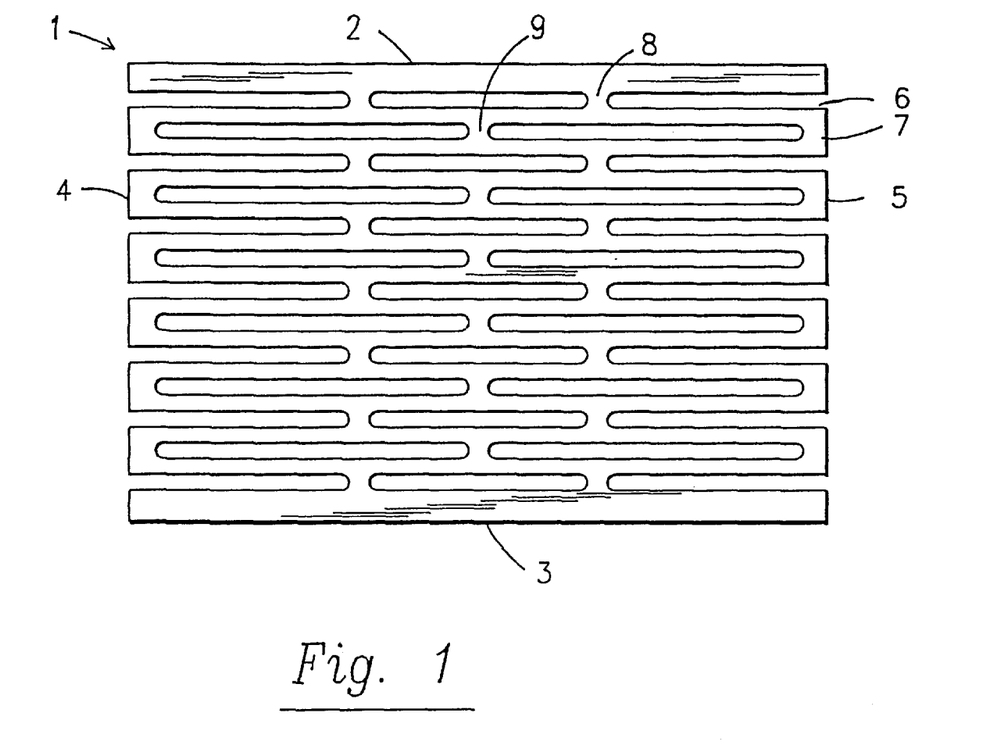
FIG. 1 shows a top view of a flat piece of material intended to be formed into a stent.
Figure 2:
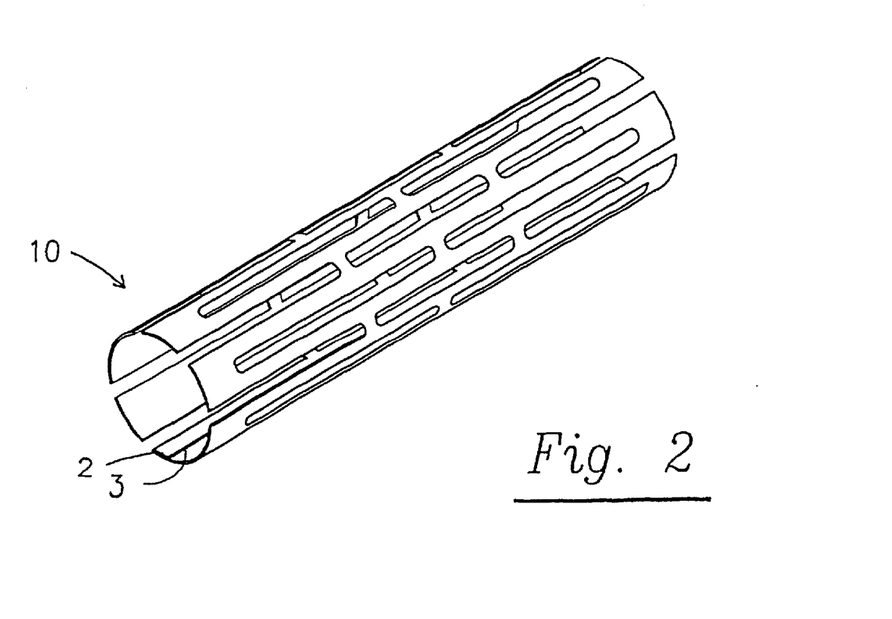
FIG. 2 shows a perspective view of the material shown in FIG. 1 formed into a stent.

With reference to FIG. 1, a flat piece of material is generally designated by the reference numeral 1 and is seen to include a top edge 2, a bottom edge 3, and ends 4 and 5. The piece of material 1 includes rows 6, 7 of slots with the rows 6 alternating with the rows 7. Spaces or solid wall portions 8 in the rows 6 between adjacent slots are staggered with respect to spaces or solid wall portions 9 in adjacent rows 7 as clearly seen in the figure. With reference to FIG. 2, the piece of material 1 is formed into a generally cylindrical stent 10 with the edges 2, 3 attached together by any suitable means such as, for example, by surface fusing, employing plasma energy, LASER or ultrasound. Of course, any suitable means for fastening the edges 2, 3 together may be employed.

Figure 3:
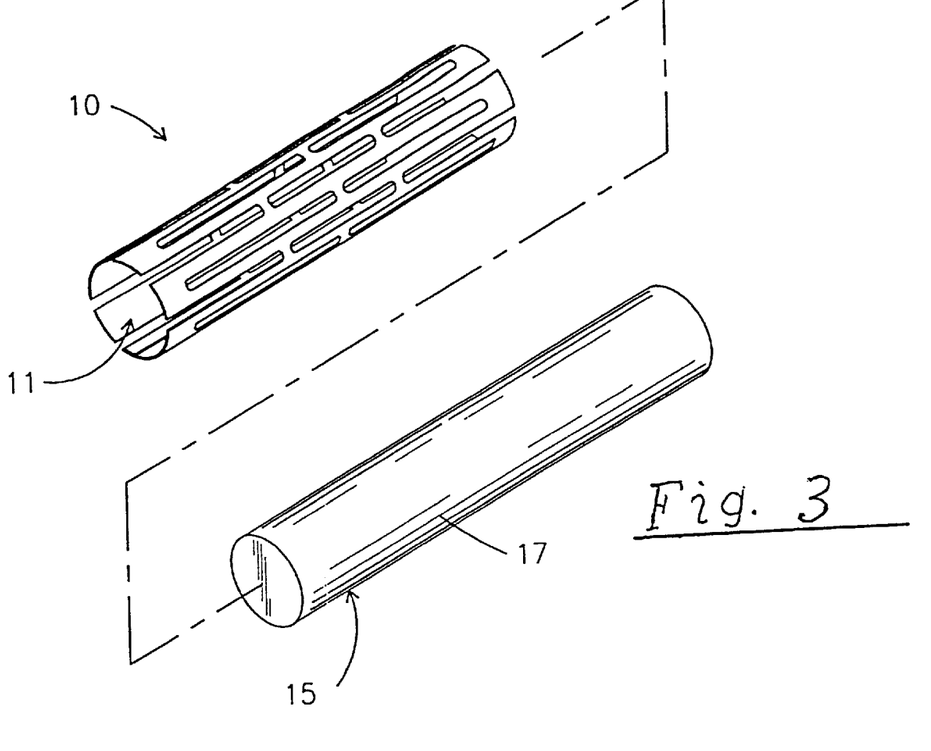
FIG. 3 shows an exploded perspective view of the stent shown in FIG. 2 with relation to a solid plastic mandrel over which it is to be placed.
Figure 4:
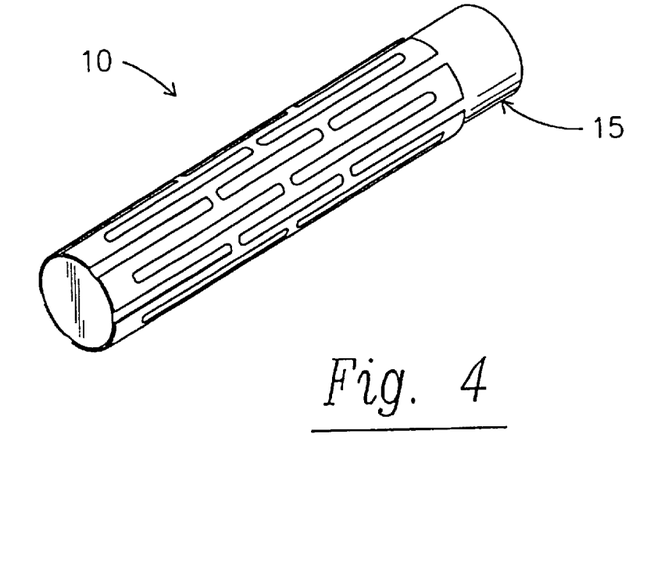
FIG. 4 shows the stent placed over the mandrel of FIG. 3.
Figure 5:
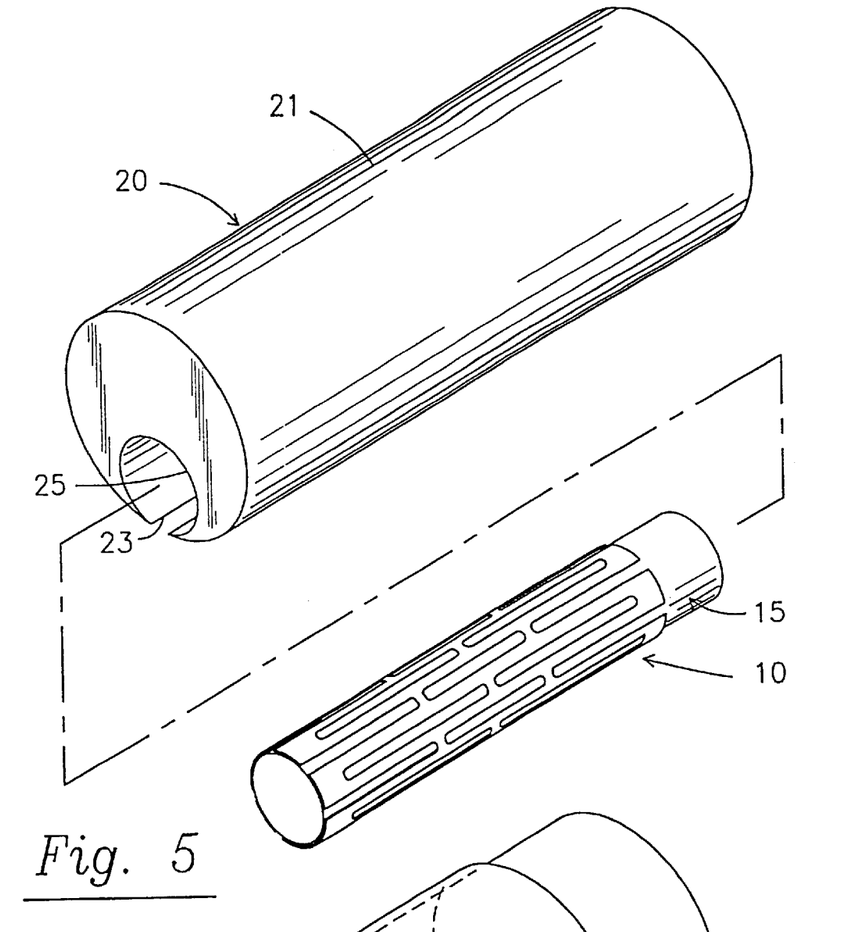
FIGS. 5 and 6 show the process of placing the stent and mandrel of FIG. 4 within a recess of a larger mandrel.
Figure 6:
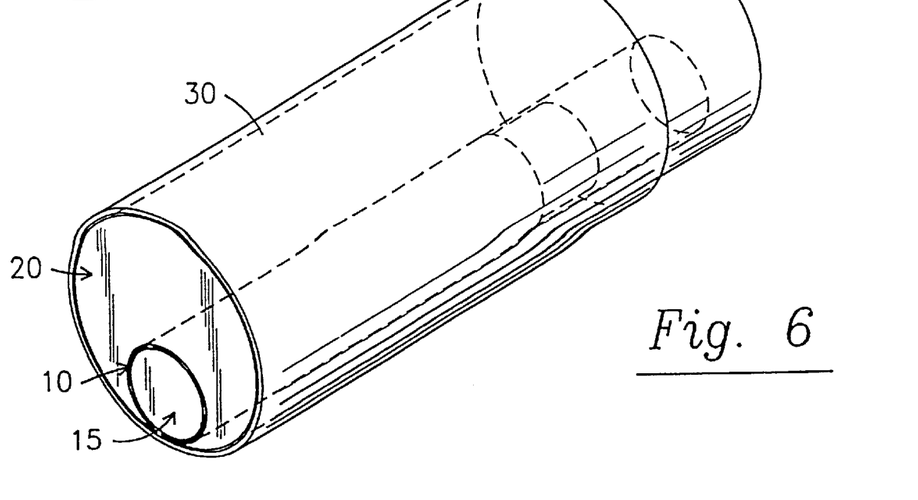
Figures 7, 8, 9:
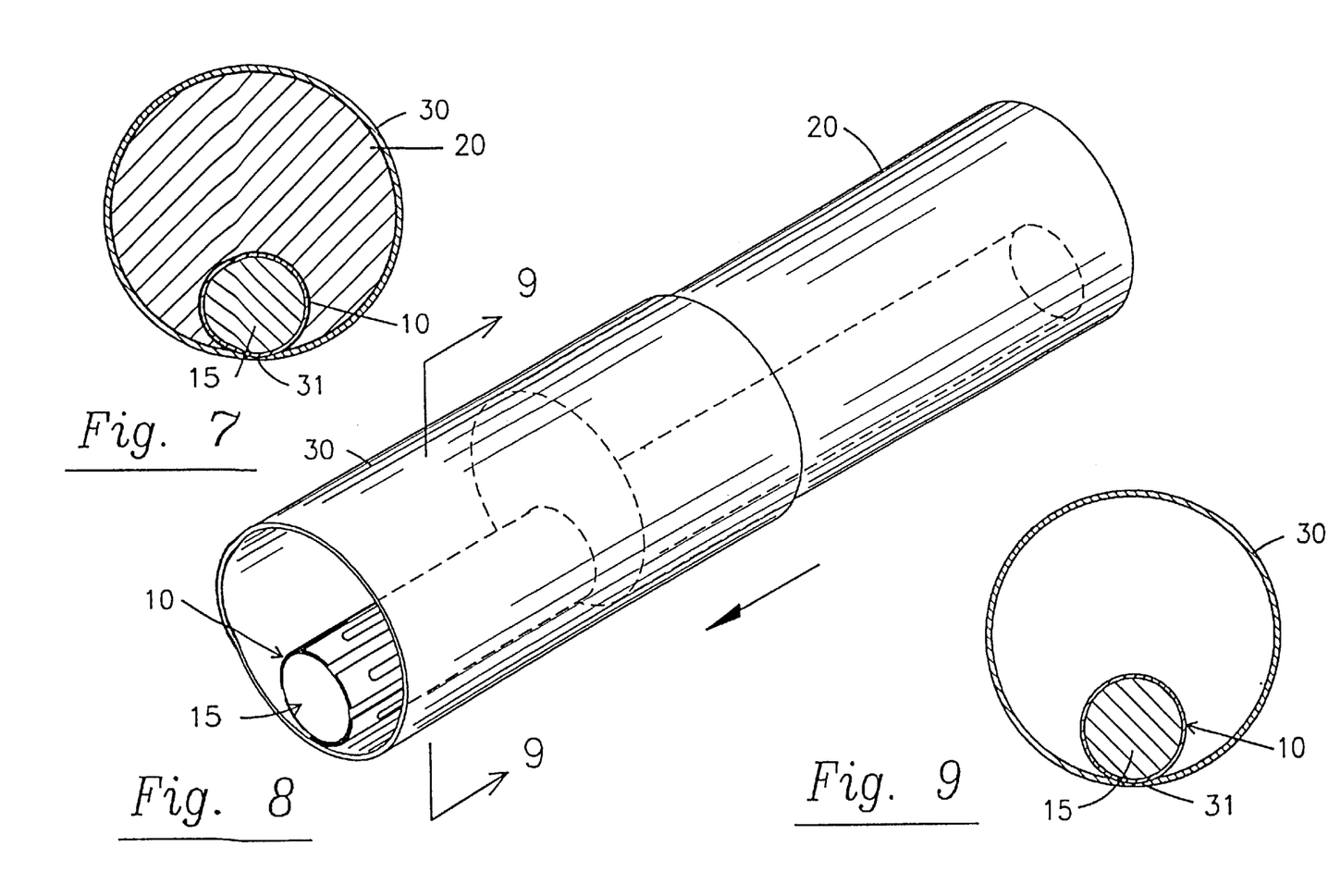
FIG. 7 shows a cross-sectional view along the line 7—7 of FIG. 6 after the coating process has taken place.
FIG. 8 shows the process of removing the coated stent from the larger mandrel.
FIG. 9 shows a cross-sectional view along the line 9—9 of FIG. 8.
Figure 12:
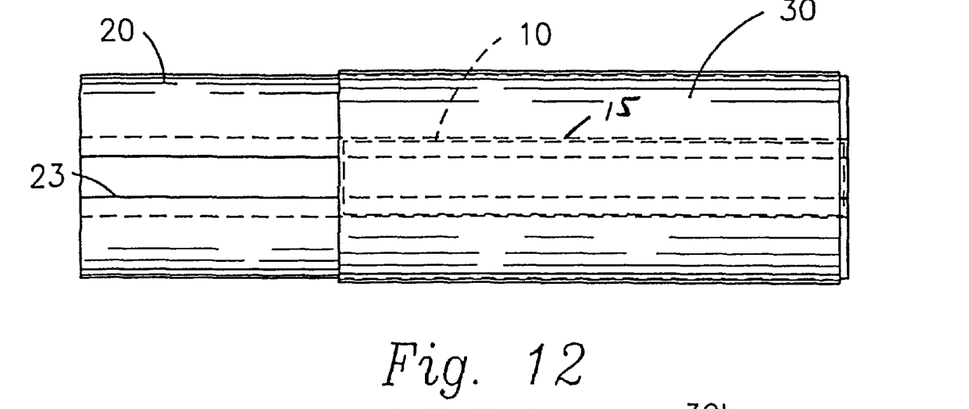
FIG. 12 shows a side view of the configuration of the stent and mandrels shown in FIG. 6.

The stent 10 may be coated, in a first inventive process, in the manner described with reference to FIGS. 3–9. As seen in FIGS. 3 and 4, the stent 10 may be placed over a solid plastic or metal generally cylindrical mandrel 15 so that the inner surface 11 of the stent 10 snugly engages the outer surface 17 of the mandrel 15 in the manner seen in FIGS. 7 and 9. With the stent 10 so mounted as best seen in FIG. 4, the stent 10 and mandrel 15 may be placed within the recess 25 of a second, larger mandrel 20 having a large generally cylindrical outer surface 21. As seen in FIGS. 5 and 7, in particular, the recess 25 is generally cylindrical in nature and is eccentrically placed with respect to the body of the second mandrel 20 so that the recess 25 intersects with the periphery of the mandrel 20 at an elongated slot 23 extending throughout the longitudinal length of the second mandrel 20. FIG. 6 shows the stent 10, the first inner mandrel 15 and the second mandrel 20 as assembled together. In the configuration shown in FIG. 6, the entire assembly is dipped in a bath of coating material so that, as best seen in FIG. 7, a coating 30 is formed about the periphery of the mandrel 20 and attaches to the stent 10 at the area designated by the reference numeral 31 in FIG. 7 that corresponds to the location of the elongated slot 23 within the mandrel 20. As should be understood, the slot 23 permits covering material to enter the recess 25 in the mandrel 20 in an elongated path along the longitudinal length of the stent 10 at one location therealong to affix the coating 30 thereto. Otherwise, the unexpanded stent 10 is uncoated. FIG. 12 shows a side view of the assembly of the coated stent 10 and the mandrels 15 and 20 as seen in FIG. 6.

FIG. 8 shows removal of the stent 10, the mandrel 15 and the coating 30 from the mandrel 20. If necessary, a lubricant may be employed for this purpose. The cross-sectional view of FIG. 9 shows the stent 10 with the coating 30 spaced therefrom except at the area designated by the reference numeral 31 where the coating 30 is firmly attached to the stent 10. Subsequently, the mandrel 15 is removed from the interior of the stent 10.

Figures 15, 16:
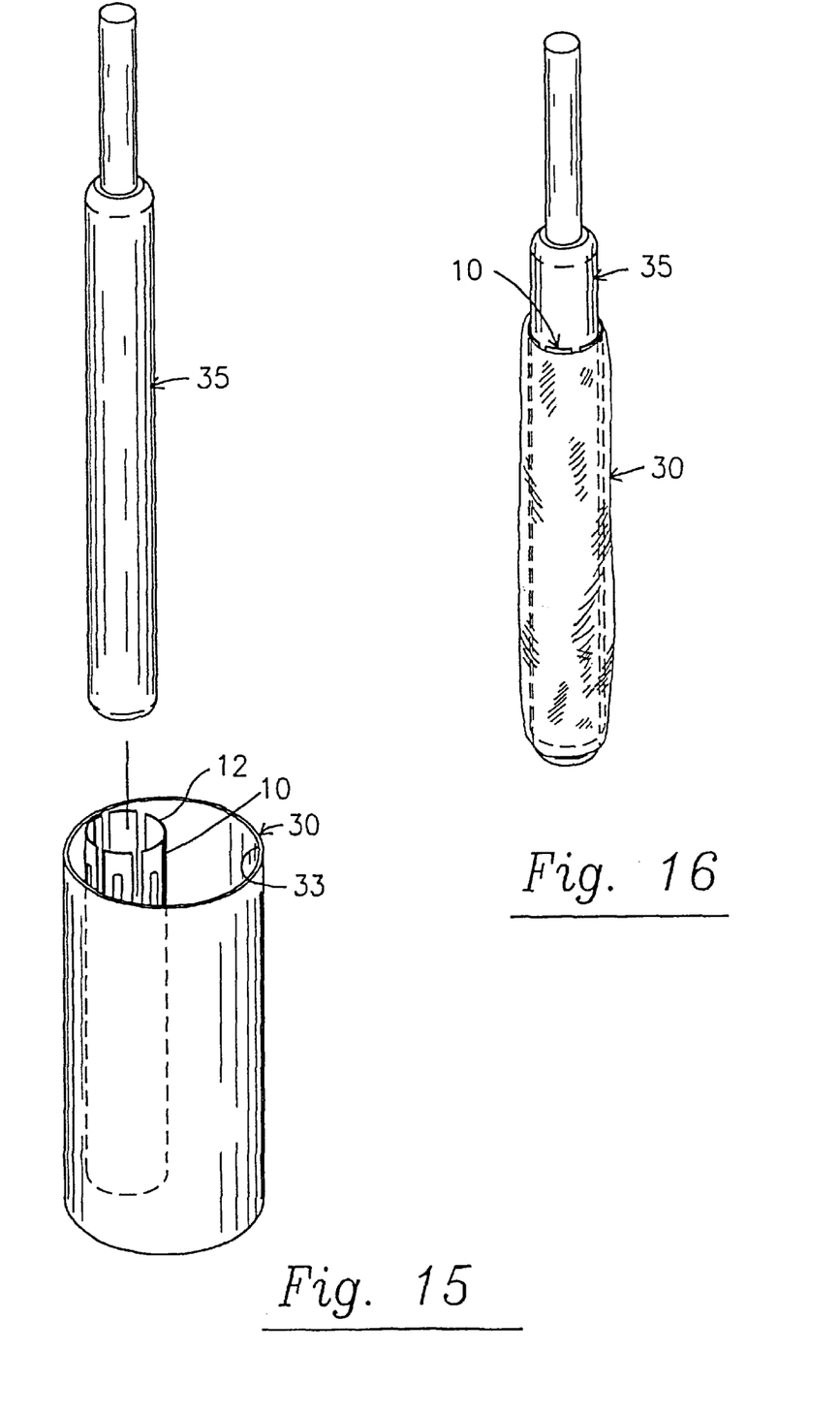
FIG. 15 shows the process of inserting a balloon catheter within the coated stent.
FIG. 16 shows the balloon catheter within the stent with the outer coating wrapped closely therearound for insertion.

With reference to FIG. 15, the coated stent 10 is used by inserting a balloon catheter 35 snugly within the unexpanded stent 10 and by loosely wrapping the coating 30 about the stent 10 so that the configuration is small enough to be easily inserted within a blood vessel as shown in FIG. 16. As should now be understood, when the balloon catheter 35 is expanded in a manner well known to those skilled in the art, the stent 10 expands so that the outer surface 12 thereof peripherally engages the inner surface 33 of the coating 30 so that, in the expanded state, the stent 10 is fully covered with a coating that has complete integrity.

Figure 10:
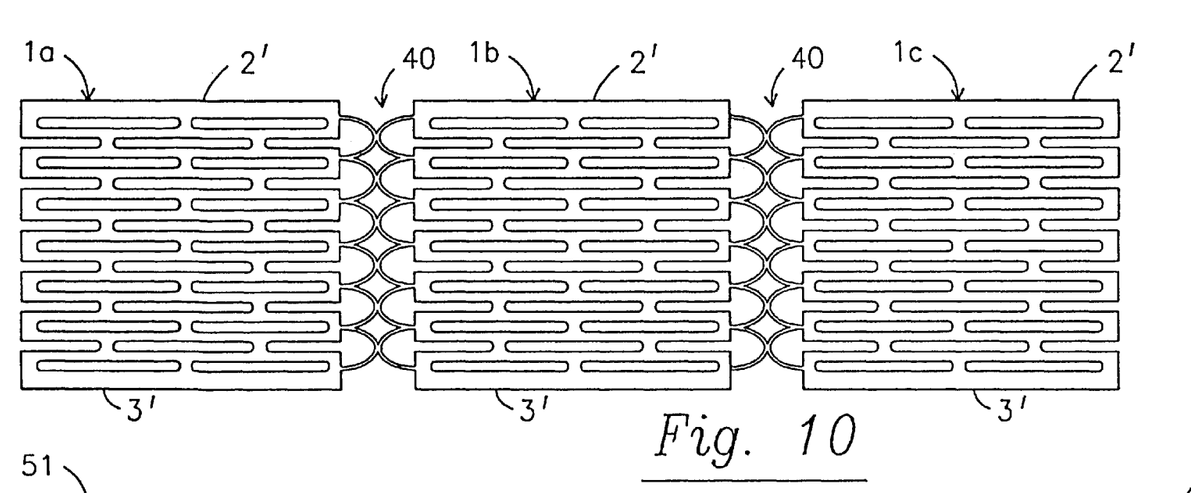
FIGS. 10 and 11 show top views of two different embodiments of stents made up of a plurality of stent sections interconnected together.

FIG. 10 shows a plurality of flat pieces 1a, 1b and 1c interconnected together by resilient flexible connectors 40, each of which consists of a series of rows of generally "X"-shaped members fixed together as shown. As should be understood, the device shown in FIG. 10 may be assembled into a triple stent by forming the entire assembly into a roll as understood with reference to FIGS. 1 and 2.

Figure 11:
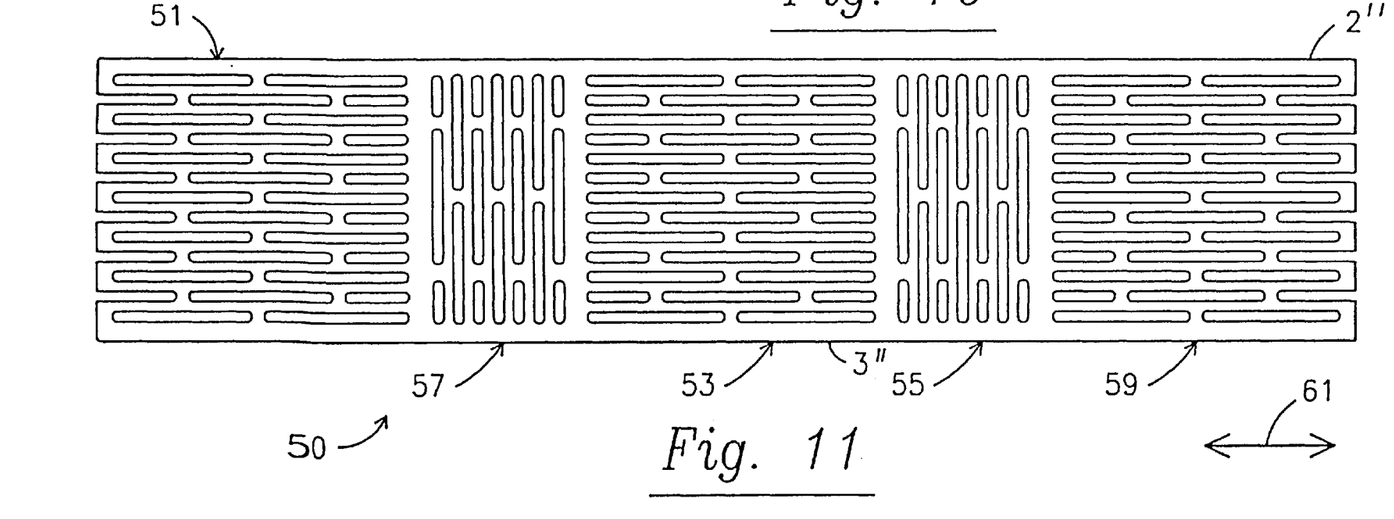

FIG. 11 shows an assembly 50 that consists of regions 51, 53 and 59, each one of which corresponds to the flat piece of material 1 as seen in FIG. 1. The members 51 and 53 are interconnected together by the connecting portion 57 while the members 53 and 59 are interconnected together by the connecting portion 55. The device 50 illustrated in FIG. 11 may be assembled into a triple stent, again, in the manner that should be understood from FIGS. 1 and 2. The connecting portions 57 and 55 allow longitudinal expansion of the length of the device 50 in the directions of the double headed arrow 61.

In the embodiments illustrated in FIGS. 10 and 11, the free edges 2', 3' and 2", 3", respectively, may be interconnected in the manner described with reference to FIG. 2.

The flat piece of material 1, 1a, 1b or 1c is manufactured by using a laser cutting tool to prepare the slots in rows 6 and 7 in either a sheet of metal or plastic. The laser tool cuts out each of the slots for rows 6 and 7 from a preprogrammed pattern. The metal can be stainless steel, titanium, nickel, a thermal alloy such as NITNOL or other metal compatible with a patient's vascular tissue. The coating 30 is a biocompatible material such as polyurethane, polyethylene, polytetrafluroethylene, silicone, block co-polymers of polyurethane, polyethylene and silicone, a biodegradable polymer such as polylactic acid, polyglycollic acid, and or hydroxy butyrate or valerate co-polymer. Biocompatible material will not interfere with blood or blood vessel interior wall tissue. The polymers can include anticoagulant agents, growth factor and like agents for reducing the reaction of blood to foreign surfaces.

Plastics employed to make the flat piece of material 1, 1a, 1b or 1c can be polyethylene, polyurethane, polytetrafluroethylene, silicone or copolymer of polyurethane and polyethylene compatible with the vascular tissue of a patient.

Figure 13:
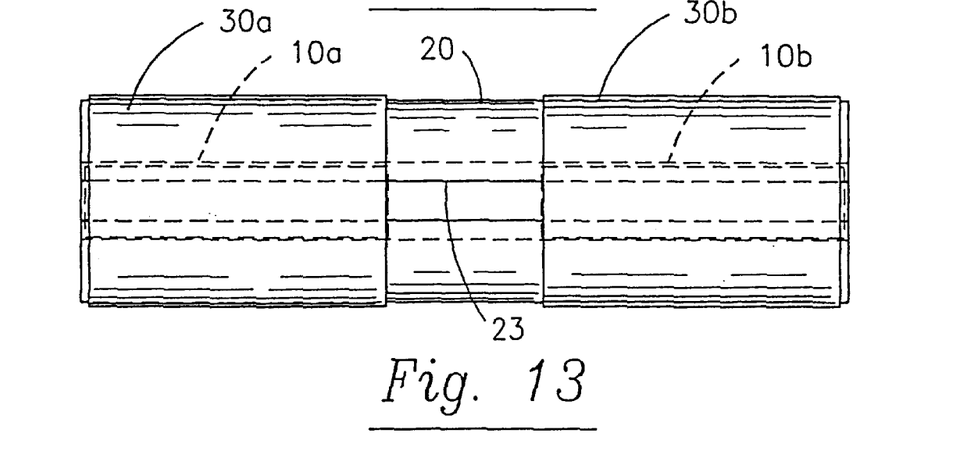
FIG. 13 shows a side view of an alternative process wherein two stents are coated on a single mandrel.
Figure 14:
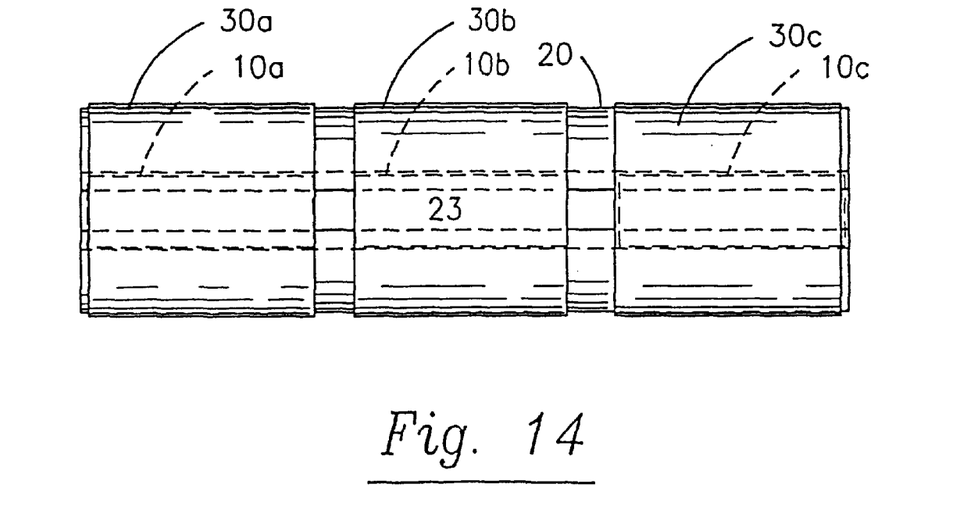
FIG. 14 shows a side view of the practicing of a further process wherein three spaced stents are coated on a single mandrel.

With reference to FIG. 12, as explained hereinabove, the mandrel 20 has been employed to create a single coated stent 10. FIG. 13 shows the use of the mandrel 20 to provide coatings 30a and 30b on two stents 10a and 10b. Alternatively, FIG. 14 shows the use of the mandrel 20 to create three coatings 30a, 30b and 30c on respective stents 10a, 10b and 10c.

Figure 17:
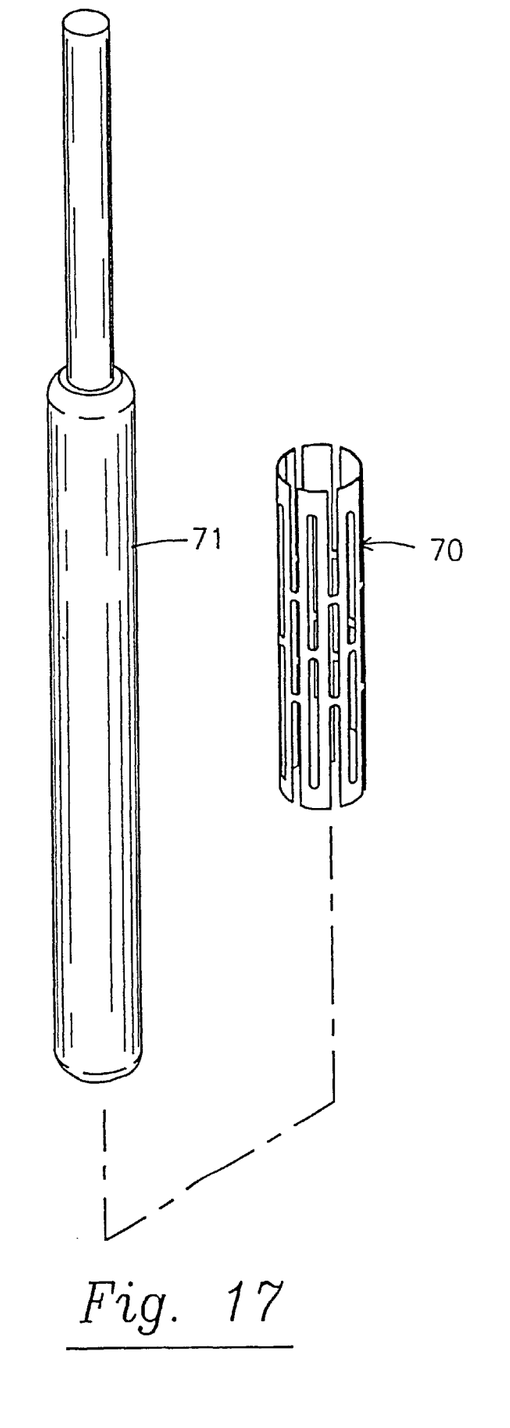
FIGS. 17 and 18 show an exploded perspective view and a perspective view, respectively, of the process for attaching a stent over a mandrel in a further process in accordance with the teachings of the present invention.
Figure 18:
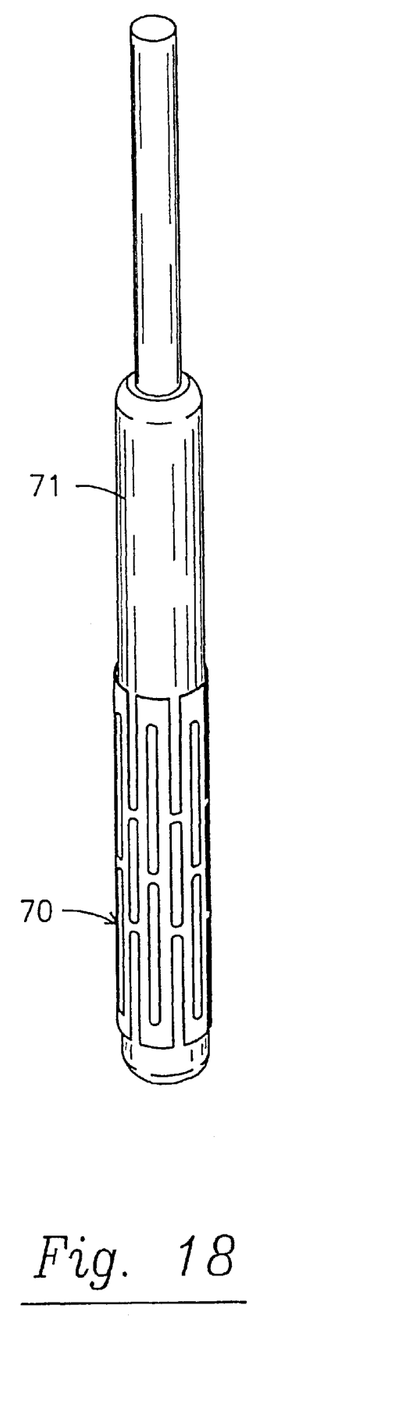
Figure 19:
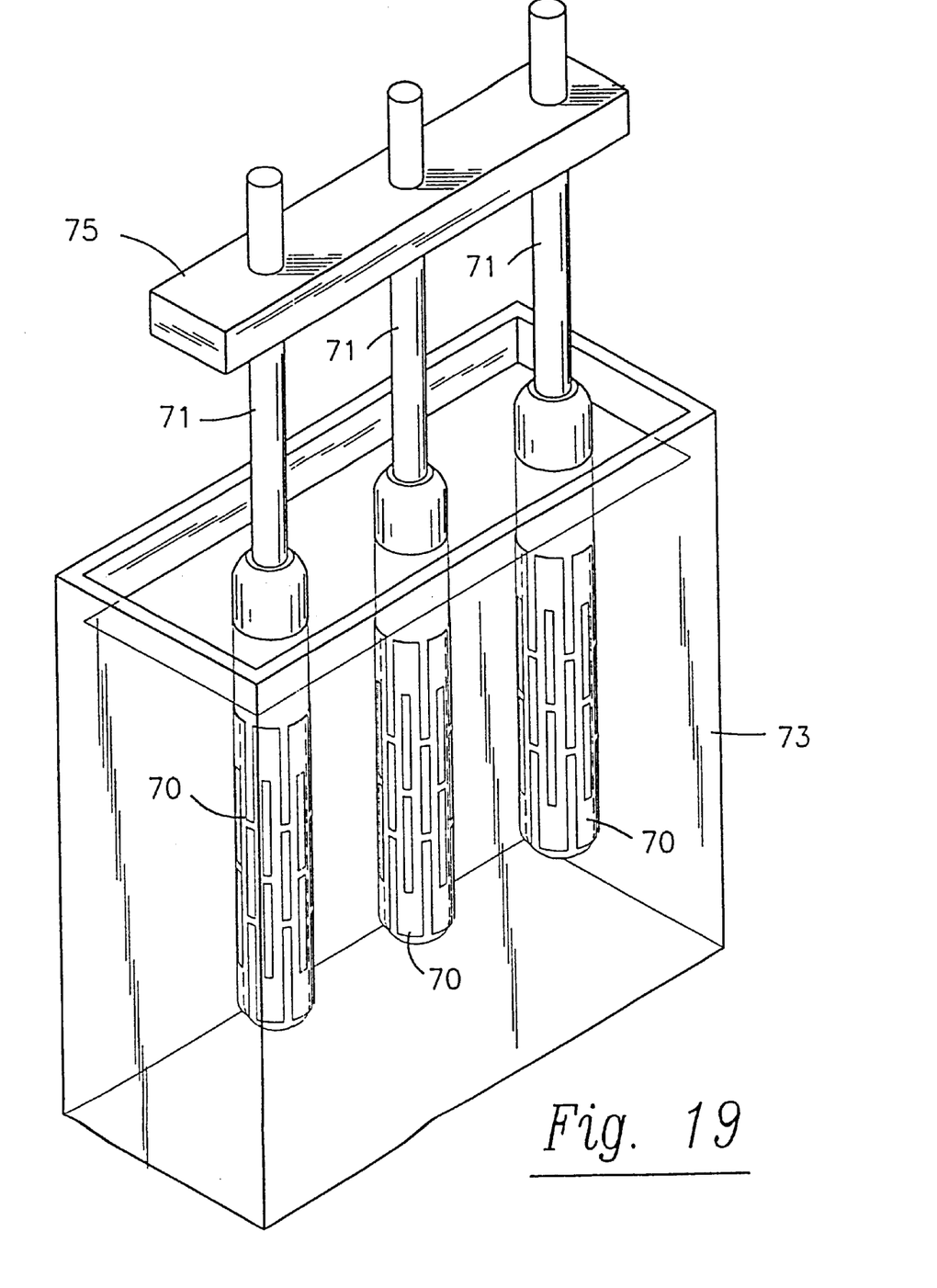
FIG. 19 shows a plurality of mandrels and stents corresponding to FIGS. 17 and 18 and suspended within a bath of coating material within a tank.
Figure 20:
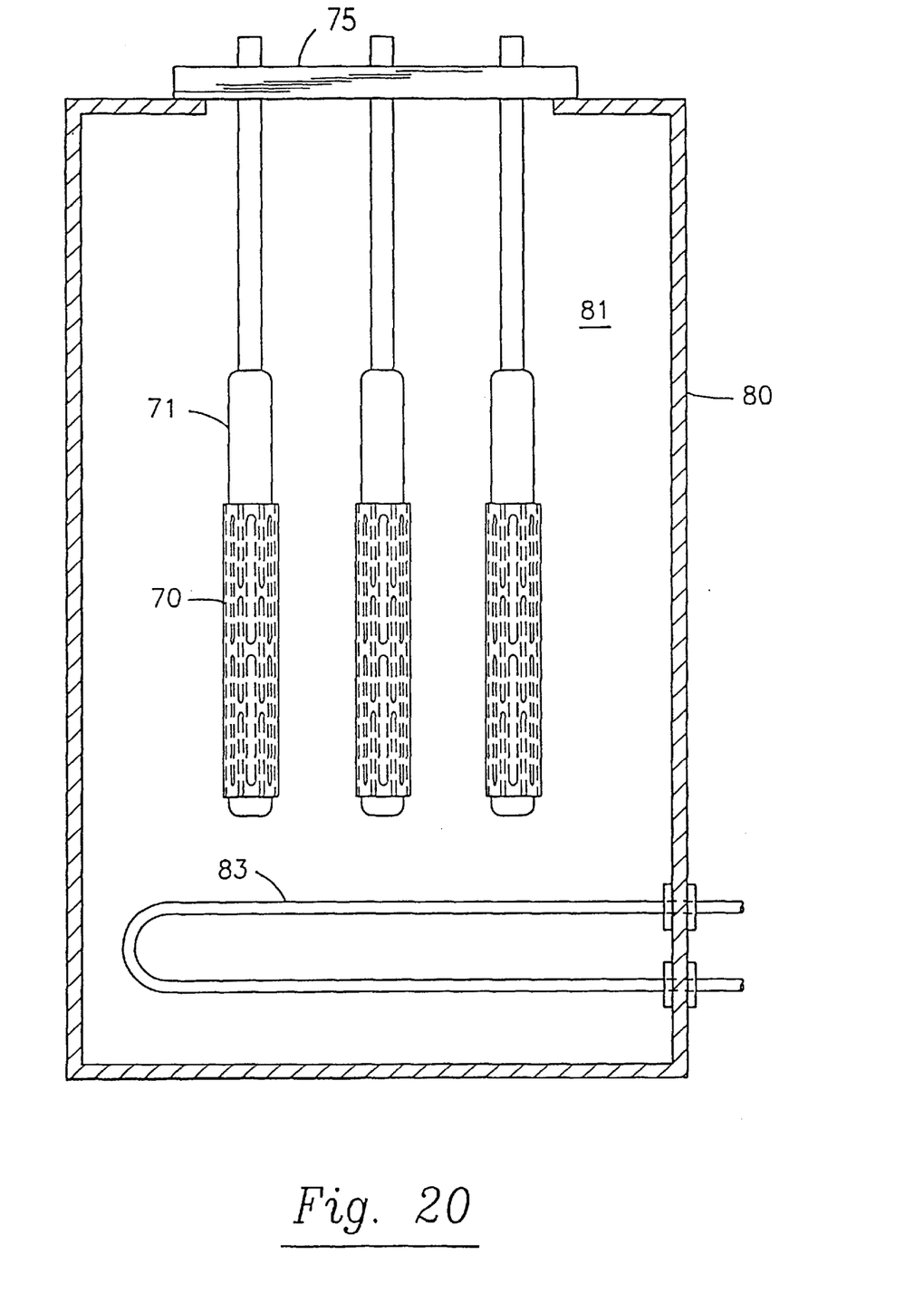
FIG. 20 shows the stents of FIG. 19, after coating, and placed within an oven to dry the coating material.
Figure 21:
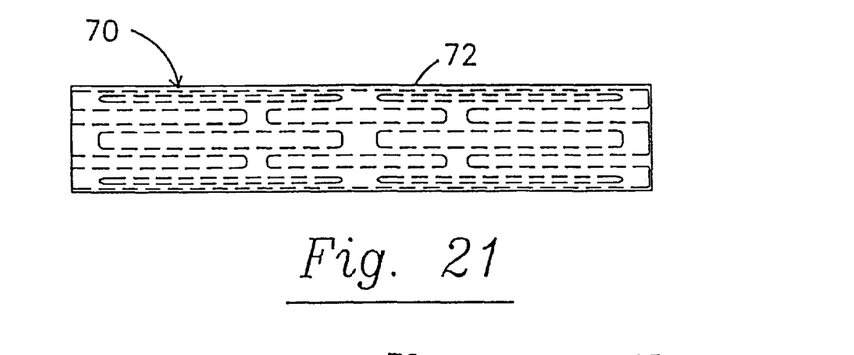
FIG. 21 shows a side view of a stent coated in accordance with the teachings of the process illustrated in FIGS. 17–20.

With reference, now, to FIGS. 17–20, a further process in accordance with the teachings of the present invention is depicted. In FIGS. 17 and 18, a stent 70 is shown that is of the type that is known as "self-expandable". Such a stent is programmed to self-expand at a particular temperature either by using the shape memory properties of the metal or by using the inherent flexibility and elasticity thereof. The stent 70 as depicted in FIGS. 17 and 18 is shown prior to the programming step. A mandrel 71 is inserted within the stent 70. Thereafter, with reference to FIG. 19, one or more stents 70 are dipped in a container 73 containing a liquid coating with the mandrels 71 being supported on a support 75 in a manner that should be well understood. For example, the container 73 may contain a polymeric coating material. After sufficient time has elapsed with the stent 70 immersed within the bath in the container 73, the stents 70 are removed from the bath, still attached to their respective mandrels 71, and are subsequently immersed within a rinse bath to remove excess coating. Thereafter, with reference to FIG. 20, the stents 70, still attached to their respective mandrels 71 which are attached to the support 75, are placed within an oven 80 having an internal chamber 81 with a heating element 83 connectable to a source of power (not shown). The stents 70 are heated to a desired temperature for a desired period of time and excess solvents are removed during the heating process. The suitably coated stent 70 with the coating 72 thereon is seen in FIG. 21.

Figure 22:
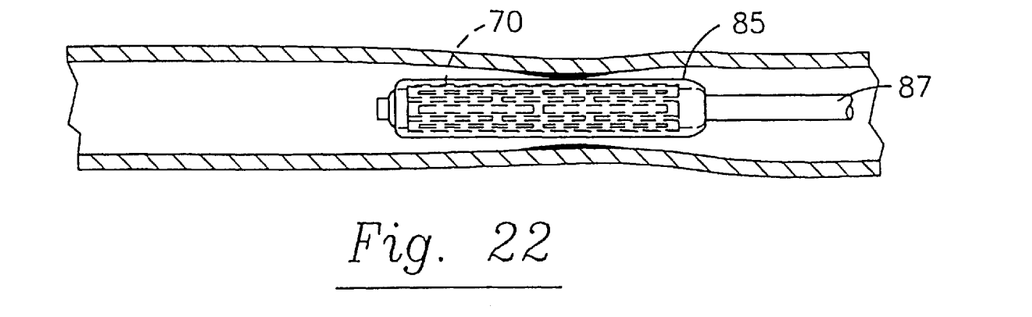
FIGS. 22, 23 and 24 show the sequential process for inserting the stent, coated in accordance with the process illustrated in FIGS. 17–20, within a blood vessel.
Figure 23:
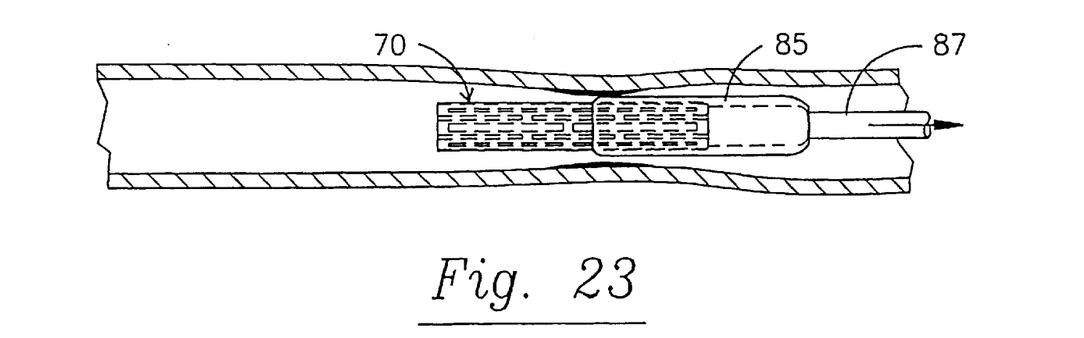
Figure 24:
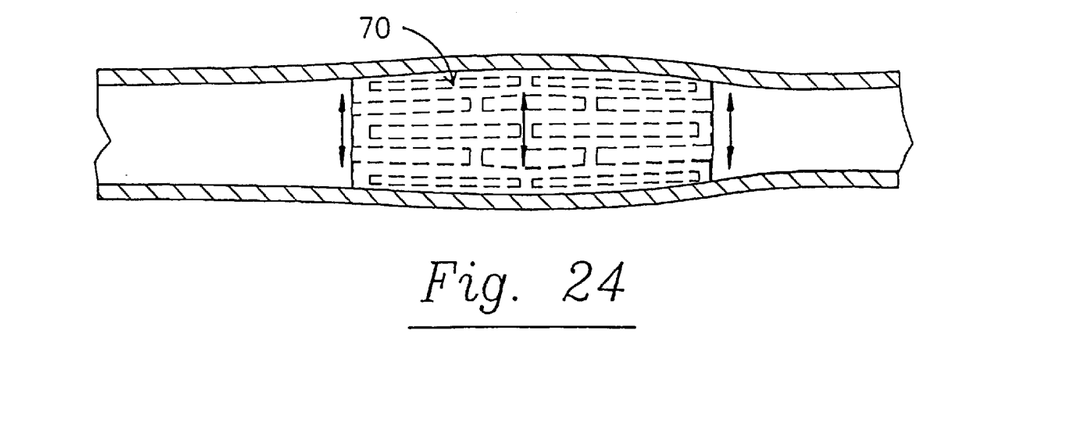

With reference to FIGS. 22, 23 and 24, a preferred method of use of the stent 70 is seen. After the process depicted in FIGS. 17–20, the stent 70 is suitably programmed. For example, the stent 70 may be dipped into a cold bath at a desired temperature and retained under cool temperature for a period of time so that when it is exposed to body temperature it expands to a desired degree of expansion. In the case of stents that are of the type that expand due to the inherent elasticity thereof, the stent is physically compressed. In either case, in the compressed state, the stent is covered with a non-expansible sheath 85 that prevents expansion until expansion is desired.

FIG. 22 shows the stent 70 encased within the sheath 85 and inserted using an appropriate mechanism 87 into a blood vessel at an appropriate location. With reference to FIG. 23, the sheath 85 is then removed and, with reference to FIG. 24, the stent 70 expands either due to its inherent elasticity or due to exposure to body temperature within the blood vessel and performs its function.

As should be understood from the above description, the process illustrated in FIGS. 17–20 may also be employed in coating the stent employing the mandrels as illustrated in FIGS. 1–9. In either case, for solvent-based polymeric coatings where the solvent can be eluted out of the material by a chemical or mechanical treatment procedure, the polymeric coating solution contains a solvent. The solvent may suitably be removed by heat (as explained with reference to FIG. 20), by vacuum or through the use of a non-solvent. If desired, several dips into the tank 73 may be carried out to provide the desired final wall thickness of the coating.

Concerning the process described with reference to FIGS. 1–9, the portion 31 of the coating where it attaches about the stent 10 may be reinforced with a line of sutures.

With further reference to the process illustrated in FIGS. 1–9, where thin wall coatings are employed that are not solvent based and which can be extruded into a very thin conduit, the conduit may be slipped onto the eccentric mandrel 20 and may be attached to the stent by welding, adhesive or by a line of sutures. Conduits that may be employed in this regard include those made of polyurethane, expanded polytetraflorol ethylene (TEFLON), extruded TEFLON, polyester which may be knit or woven, velour or non-velour, extruded, PET, PE, hydrogels that can impart a desirable elastic nature to the walls of the coating. These choices are merely given by way of example.

Additionally, biological materials such as collagen, gelatin and the like may be suitably employed. In the case of "self-expanding" stents such as the stent 70, the coating material may be solvent based, extruded or biological and may be assembled to the mandrel and attached to the "self-expanding" stent either by a continuous suture or intermittently placed sutures along one axis of the stent or by an adhesive or any other mechanical, thermal or chemical treatment that ensures attachment. The stent and the coating material are together programmed to expand at body temperature. For example, the stent and coating may be dipped in a cold bath with the coating attached to reduce them both to a much smaller size which may then be inserted into a sheath which may be removed within the body to allow expansion to the expanded size when the coating was originally applied.

Hereinabove, the use of a hydrogel material for the coating was suggested. Such a material is especially effective since it is very pliable and elastic and has an extremely slippery surface allowing easy removal from the overlying sheath.

As such, an invention has been disclosed in terms of preferred embodiments thereof which fulfill each and every one of the objects of the invention as set forth hereinabove and provide a new and useful polymer coated microporous stent and method of coating of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A method of coating a stent including the steps of:
   a) providing a tubular stent having a multi-slotted peripheral wall;
   b) inserting a first tubular mandrel into said stent;
   c) inserting said stent and first tubular mandrel into a recess formed in a second mandrel, said second mandrel having an outer periphery intersecting with said recess at a slot;
   d) dipping said stent with said first and second mandrels into a coating bath to coat said outer periphery of said second mandrel with a coating;
   e) causing said coating to enter said slot and adhere to said stent peripheral wall at a location adjacent said slot;
   f) removing said stent and mandrels from said bath; and
   g) removing said stent from said mandrels, said stent having said coating affixed thereto at said location.

2. The method of claim 1, further including the step of forming said first and second mandrels of generally cylindrical shapes.

3. The method of claim 2, further including the step of locating said recess eccentrically with respect to an axis of elongation of said second mandrel.

4. The method of claim 1, further including the step of applying continuous sutures or intermittently placed sutures at said location.

5. The method of claim 1, further including the step of providing said recess with an elongated linear configuration.

6. A method of coating a preprogrammable self-expandable stent including the steps of:
   a) providing a preprogrammable self-expandable tubular stent having a multi-slotted peripheral wall prior to programming;
   b) inserting a mandrel through said stent;
   c) coating said stent to form a coated stent;
   d) programming said coated stent to expand at a desired temperature.

7. The method of claim 6, further including the step, after said programming step, of covering said coated stent with a removable sheath.

* * * * *